United States Patent [19]

Stringer et al.

[11] Patent Number: 5,723,500
[45] Date of Patent: Mar. 3, 1998

US005723500A

[54] ANTIPLAQUE ORAL COMPOSITION AND METHOD

[75] Inventors: Orum D. Stringer, Yardley, Pa.; John C. Brahms, Trenton, N.J.; Malathy Subramanian, Branchburg, N.J.; Ernest E. Kelly, New Brunswick, N.J.

[73] Assignee: Colgate-Palmolive Company, New York, N.Y.

[21] Appl. No.: 649,389

[22] Filed: May 17, 1996

[51] Int. Cl.$^6$ .......................... A01N 31/08; A61K 31/05
[52] U.S. Cl. .................. 514/736; 514/734; 514/731; 424/49
[58] Field of Search ...................... 514/731, 734, 514/736; 424/49

[56] References Cited

U.S. PATENT DOCUMENTS

| | | | |
|---|---|---|---|
| 3,800,051 | 3/1974 | Barnhart et al. | 424/346 |
| 4,321,257 | 3/1982 | Sipos | 424/80 |
| 5,188,821 | 2/1993 | Gaffar et al. | 424/52 |
| 5,487,893 | 1/1996 | Vachy | 424/195.1 |

FOREIGN PATENT DOCUMENTS

| | | |
|---|---|---|
| 2128026 | 10/1972 | France . |
| 553142 | 8/1974 | Switzerland . |
| 9210992 | 7/1992 | WIPO . |

OTHER PUBLICATIONS

Chemical Abstracts vol. 93, No. 17, Oct. 27, 1980.
(Abstract No. 162715—Japan Kokai 55 016 802—Ajinomoto).

Primary Examiner—Marianne M. Cintins
Assistant Examiner—Dwayne C. Jones
Attorney, Agent, or Firm—Henry S. Goldfine

[57] ABSTRACT

An oral antiplaque composition and treatment of teeth therewith wherein the essential antiplaque agent is a substantially water insoluble noncationic antibacterial phenol containing, relative to the hydroxyl group, an alkyl or cycloalkyl group, preferably tert.-butyl (t-butyl), in 2-position, and substituents in one or both of the 4- and 5-positions, one of which may be phenyl or 2', 3' and/or 4' substituted alkyl or cycloalkyl phenyl, preferably 4'-t-butyl phenyl or a phenanthrene containing a hydroxyl substituent in the 2- or 3-position and alkyl or cycloalkyl, preferably t-butyl, substituents in the other of the 2- and 3-positions and in at least one of the other rings. Novel antibacterial alkylated phenols are also described.

46 Claims, No Drawings

ANTIPLAQUE ORAL COMPOSITION AND METHOD

BACKGROUND OF THE INVENTION

Field of the Invention

This invention relates to antibacterial antiplaque oral compositions and also to compositions containing a novel essential antiplaque component comprising a substantially water insoluble, noncationic antibacterial alkylated phenol compound more fully described below and to a selected group of such compounds which are considered novel.

Dental plaque is a soft deposit which forms on teeth as opposed to calculus which is a hard calcified deposit on teeth. Unlike calculus, plaque may form on any part of the tooth surface, particularly including at the gingival margin. Hence, beside being unsightly, it is implicated in the occurence of gingivitis.

Accordingly, it is highly desirable to include antimicrobial (antibacterial) agents which have been known to reduce plaque in oral compositions.

The cationic antibacterial materials such as chlorhexidine, benzthonium chloride and cetyl pyridinium chloride have been the subject of greatest investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions.

Halogenated hydroxydiphenyl ethers such as triclosan have been very effectively employed in oral compositions as antibacterial antiplaque agents. However, it is desirable to be able to provide non-halogenated agents which are highly effective and possibly even more effective than triclosan.

Phenol and alkyl substituted phenols are well known and widely used antimicrobials. Thymol (2-isopropyl-5-methylphenol) is an active antimicrobial agent in commercial mouthrinse formulations, but its anti-microbial activity is considered relatively low and possibly insufficient, its activity for example being only a small fraction of the activity of triclosan. Hitherto, alternatives to triclosan having substantially greater antiplaque activity than thymol or than monoalkyl phenols and optimally comparable to or even greater then the activity of triclosan have not been available.

It is an object of this invention to provide an antiplaque oral composition with substantial antiplaque effectiveness containing noncationic phenolic oral antibacterial antiplaque agents (AA) as alternatives to triclosan. Another object is to provide alkyl phenolic AA's which, except for the single OH group, are entirely hydrocarbon and which have oral antimicrobial activities up to 100 or more times the activity of thymol, for instance up to as much as or exceeding the activity of triclosan. A further object is to provide such AA's which are, or can be expected to be, found in nature, e.g. plant material, etc. Still another object is to provide novel AA's. Other objects and advantages will appear as the description proceeds.

SUMMARY OF THE INVENTION

In accordance with some of its aspects, this invention relates to an oral antiplaque composition comprising an orally acceptable vehicle and an effective antiplaque amount of at least one substantially water insoluble noncationic monohydroxy AA having one of the following formulae:

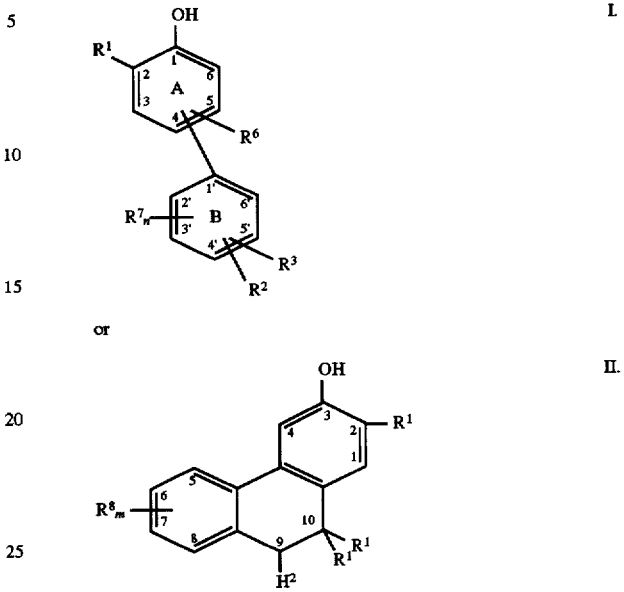

wherein $R^1$ is (1) a $C_{1-8}$ n-alkyl, optionally partially or fully substituted with $C_{3-6}$ cycloalkyls or $C_{1-7}$ side chain alkyls, or (2) a $C_{3-6}$ cycloalkyl, optionally partially or fully substituted with $C_{1-7}$ side chain alkyls or $C_{3-6}$ cycloalkyls;

the B ring and $R^6$ of formula I are interchangeably substituted in the 4 and 5 positions of the A ring of formula I, and $R^6$ is H or $R^1$; and (1) $R^2$ and $R^3$ are interchangeably substituted in the 4' and 5' positions of the B ring of formula I, $R^2$ is $R^1$ and $R^3$ is H or $R^1$; or (2) in the B ring, $R^3$ in the 5'-position is H, $R^2$ in the 4' position is $R^7$, $R^7$ is independently H or $R^1$ in the 2' and/or 3' positions, and n is 2; and $R^8$ in formula III is independently H or $R^1$ in the 5, 6, 7 and/or 8 positions and m is 4.

We have further found that in the vast majority of instances, highly and unexpectedly superior antimicrobial activity is supplied by AA's of one of the above formulae containing t-butyl (tert-butyl) as at least one and preferably two (or even or more) of the $R^1$ and $R^4$ values.

This invention is at least in part based on our further findings that:

1. tert-butyl (t-butyl) substitution at the ortho position of an unsubstituted phenol can enhance its antimicrobial effect by a factor of 10.

2. tert-butyl substitution of the pendant phenyl group of a phenylphenol (formula I), e.g., substitution of 2-tert-butyl-5-phenyl phenol to give 2-tert-butyl-5-(4'-tert-butylphenyl) phenol likewise enhances the activity of the resultant by an additional factor of 10.

Thus, for instance, 3-phenyl phenol (3-hydroxybiphenyl) has an activity slightly less than that of thymol vs. *A. viscoscus*, a common constituent of human dental plaque. On the other hand, 2-tert-butyl-5-phenyl phenol (3-hydroxy-4-tert-butylbiphenyl) has an observed activity 50 times greater than thymol and 2-tert-butyl-5-(4'-tert-butylphenyl) phenol (3-hydroxy-4,4'-di-tert-butylbiphenyl) has an observed activity greater than 100 times that of thymol.

As described herein other alkyl phenol AA's also provide enhanced antibacterial effectiveness for prevention or reduction of plaque formation.

By way of further example, phenols of the type

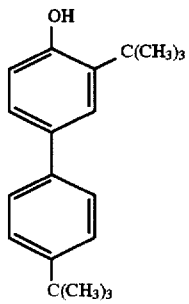

2-t-butyl-4-(4'-t-butylphenyl)phenol

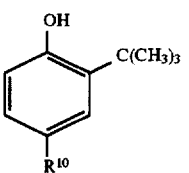

2-t-butyl-4-R¹⁰-phenol
wherein R¹⁰ = phenyl and

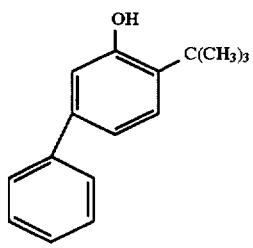

2-t-butyl-5-phenylphenol can to have an activity level at least 10× that of thymol.

Phenols of the type:

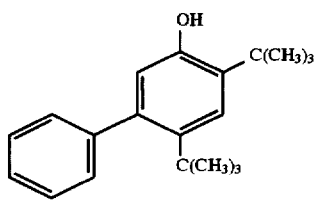

2,4-di-t-butyl-5-phenylphenol

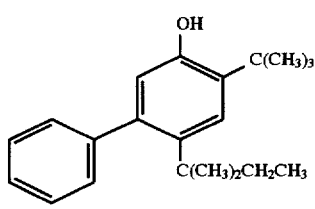

2-t-butyl-4-(1,1-dimethylpropyl)-5-phenylphenol

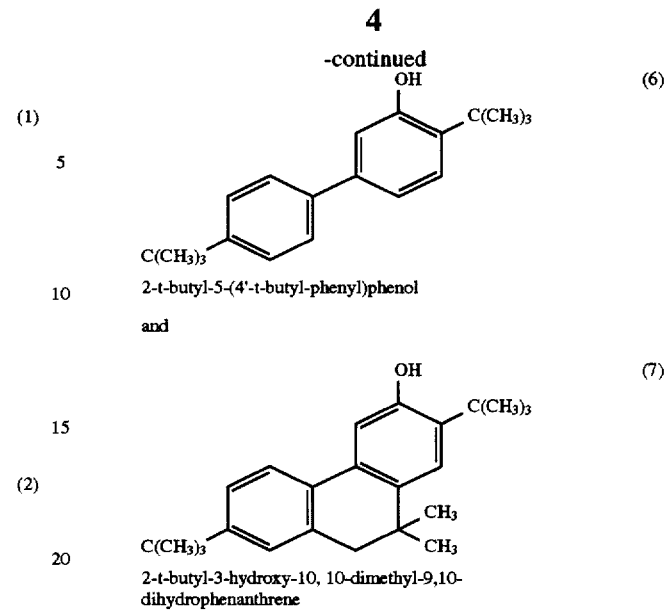

2-t-butyl-5-(4'-t-butyl-phenyl)phenol and 2-t-butyl-3-hydroxy-10,10-dimethyl-9,10-dihydrophenanthrene can have an activity level in the range 100× thymol. This is the activity level of triclosan.

The above AA compounds (1)–(7) fall within the scope of the AA agents of formulas I and, II and it will be understood that related compounds active as AA agents can be employed containing indicated variations in values, numbers and positions of $R^1$ and $R^6$–$R^8$, as for example:

2-methyl-5-(4'-cyclopropylphenyl)phenol
2-octyl-5-(4'-cyclohexylphenyl)phenol
2-cyclohexyl-5-(4'-isopropylphenyl)phenol
2,4-diisopropyl-5-phenylphenol
2,4-dicyclopropyl-5-phenylphenol
2,4-dimethyl-5-phenylphenol
2-t-butyl-5(4'-isopropylphenyl)phenol
2-t-butyl-4(4'-cyclohexylphenyl)phenol
2-t-butyl-4-(1,1-dimethyloctyl)5-phenylphenol
2-(1-cyclopropylbutyl)-4-t-butyl-5-phenylphenol
2-isopropyl-4-phenylphenol
2-cyclobutyl-4-phenylphenol
2-ethyl-4-phenylphenol
2-isooctyl-5-phenylphenol
2-cyclopropyl-5-phenylphenol
2-methyl-5-phenylphenol
2-(1-t-butylhexyl)-5-phenylphenol
2-t-butyl-3-hydroxy-10,10-di-t-butyl-9,10-dihydrophenanthrene
2-(1,1-dimethylpropyl-3-hydroxy-10,10-di-cyclohexyl-9,10-dihydrophenanthrene While 2-tert-butyl-5-phenyl phenol (3-hydroxy-4-tert-butylbiphenyl) is known, it's use as an antimicrobial is not believed to have been reported in the literature. The same applies to a number of other compounds of any of the above formulae, for instance formula I. As described below, a number of the AA's are also novel.

The improved antimicrobial activities attainable in accordance with this invention generally involves use of branched in preference to straight chains, selective positioning of substituents, increased numbers of substituents and/or the carbon content of alkyl substituents. The improved antimicrobial activities are unexpected, particularly in view of teachings to the contrary in the prior art. For example, C. M. Suter, Chem. Rev. 28 269–299(1941), in discussing phenol coefficients of alkylphenols v. B. typhosus and Staph. aureus, states (a) "the position of the alkyl group has no effect", and (b) "the o- and p-sec-butyl phenols have phenol coefficients of 28, and the branching of the carbon side chain, as in tert.butylphenol, reduces the effectiveness to about 20" (p. 272), and also (c) "the generalization that the straight-chain primary alkylphenols are more effective than their isomers" (p. 273), "(d) It was concluded that the isobutyl compounds were probably less effective than their n-butyl isomers", and also (e) "As in the alkylphenols, branching of the carbon chain reduces the effectiveness" (p. 275). The microorganisms employed in the above-quoted situations were not those generally encountered in the oral cavity.

Evans et al. J. Periodontol. 48, 156–162 (1977) in an article entitled "In Vitro Antiplaque Effects of Antiseptic Phenols" concludes that whereas "3,5,4'-tribromosalicylanilide was found to be effective against growth and plaque formation of *A. viscosus, A. naeslundii, S. mutans* and *S. sanguis*, Dibromsalicil was found effective against *A. viscosus*. The other phenols (hexylresorcinol, thymol, phenylphenol and zinc phenolsulfonate) did not inhibit in vitro growth or plaque formation".

It will be understood that in the above formulae I and II of the AA's employed in the oral compositions of this invention, the $C_{1-7}$ and $C_{1-8}$ side chain and n-alkyls range from methyl to heptyl and octyl and the $C_{3-6}$ cycloalkyls range from cyclopropyl to cyclohexyl. These AA's generally range in molecular weight (M.W.) from about 175 to about 500, preferably about 190 to about 350, more preferably about 210 to about 310. The AA is employed in the oral compositions of the invention in a non-toxic, effective antiplaque amount, typically in a range of about 0.003–5%, preferably about 0.005–3%, more preferably about 0.02–1%. The pH of the oral compositions of this invention may range from about 4.0 to about 9.0.

To increase substantivity and enhance the antibacterial activity of the AA even more, an antibacterial enhancing agent (AEA) may be included in the oral composition. The use of AEA's in combination with water-insoluble noncationic antibacterial compounds is known to the art, as for example U.S. Pat. No. 5,188,821 and 5,192,531. An AEA agent is an organic material which contains a delivery-enhancing group and a retention-enhancing group. As employed herein, the delivery-enhancing group refers to one which attaches or substantively, adhesively, cohesively or otherwise bonds the AEA agent (carrying the AA compound) to oral (e.g. tooth and gum) surfaces, thereby "delivering" the compound to such surfaces. The organic retention-enhancing group, generally hydrophobic, attaches or otherwise bonds the AA to the AEA, thereby promoting retention of the AA to the AEA and indirectly on the oral surfaces. The enhanced retention of the AA on the oral surfaces results in an improvement in the retardatoin of plaque growth on oral surfaces.

Preferably, the AEA is an anionic polymer comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferably otherwise bonded to atoms, preferably carbon, in the chain.

The AEA may be a simple compound, preferably a polymerizable monomer, more preferably a polymer, including for example oligomers, homopolymers, copolymers of two or more monomers, ionomers, block copolymers, graft copolymers, cross-linked polymers and copolymers, and the like. The AEA may be natural or synthetic, and water insoluble or preferably water (saliva) soluble or swellable (hydratable, hydrogel forming) having an (weight) average molecular weight of about 100 to about 5,000,000, preferably about 1,000 to about 1,000,000, more preferably about 25,000 to 500,000.

In the case of the polymeric AEA's, it is desirable, for maximizing delivery and retention of the AA to oral surfaces, that the repeating units in the polymer chain or back-bone containing the acidic delivery enhancing groups constitute at least about 10%, preferably at least about 50%, more preferably at least about 80% up to 95% or 100% by weight of the polymer.

The AEA generally contains at least one delivery-enhancing group, which is preferably acidic such as sulfonic, phosphinic, or more preferably phosphonic or carboxylic, or a salt thereof, e.g. alkali metal or ammonium and at least one organic retention-enhancing group, such typically groups having the formula $-(X)_n-R$ wherein X is O, N, S, SO, SO2, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents on R which are generally non-hydrophilic and do not significantly interfere with the desired function of the AEA as enhancing the delivery of the AA to and retention thereof on oral surfaces such as halo, e.g. Cl, Br, I, and carbo and the like. Illustrations of such retention-enhancing groups are tabulated below.

| $-n$ | X | $-(X)_nR$ |
|---|---|---|
| 0 | — | methyl, ethyl, propyl, butyl, isobutyl, t-butyl cyclohexyl, allyl, benzyl, phenyl, chlorophenyl, xylyl, pryridyl, furanyl, acetyl, benzoyl, butyryl, terephthaloyl. |
| 1 | O | ethoxy, benzyloxy, thioacetoxy, phenoxy, carboethoxy, carbobenzyloxy. |
| | N | ethylamino, diethylamino, propylamido, benzylamino, benzoylamido, phenylacetamido. |
| | S | thiobutyl, thioisobutyl, thioallyl, thiobenzyl, thiophenyl, thiopropionyl, phenylthioacetyl, thiobenzoyl. |
| | SO | butylsulfoxy, allylsulfoxy, benzylsulfoxy, phenylsulfoxy. |
| | $SO_2$ | butylsulfonyl, allylsulfonyl, benzylsulfonyl, phenylsulfonyl. |
| | P | diethylphosphinyl, ethylvinylphosphinyl, ethylallylphosphinyl, ethylbenzylphosphinyl, ethylphenylphosphinyl. |
| | PO | diethylphosphinoxy, ethylvinylphosphinoxy, methylallylphosphinoxy, methylbenzylphosphinoxy, methylphenylphosphinoxy. |
| | Si | trimethylsilyl, dimethylbutylsilyl, dimethylbenzylsilyl, dimethylvinylsilyl, dimethylallylsilyl. |

Preferably, the AEA is a natural or synthetic anionic polymeric polycarboxylate having a molecular weight of about 1,000 to about 5,000,000, preferably about 30,000 to about 500,000.

The synthetic anionic polymeric polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride haviing a molecular weight (M.W.) of about 30,000 to about 1,000,000, most preferably about 30,000 to about 500,000. These copolymers are available, for example, as Gantrez®, e.g. AN 139 (M.W. 500,000), AN 119 (M.W. 250,000); and preferably S-97 Pharmaceutical Grade (M.W. 70,000), of GAF Corporation.

Other polymeric polycarboxylates containing or modified to contain retention enhancing groups operative in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA® No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative polymeric polycarboxylates containing or modified to contain retention enhacing groups include copiolymers of maleic anhydride with styrene, isobutylene or ethyl vinyl either, polyacrylic, polyitaconic and polymaleic acids, and sulfonacrylic oligomers of M.W. as low as 1,000 available as Uniroyal® ND-2.

Also suitable for use in the practice of the present invention are polymerized olefinically or ethylenically unsaturated carboxylic acids containing an activated carbon-to-carbon olefinic double bond which readily functions on polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, betastyrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

Also useful in the practice of the present invention are so-called carboxyvinyl polymers. They are commercially available, for example, under the trademarks Carbopol® 934, 940 and 941 of B. F. Goodrich, these products consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4–5 million or more.

Illustrative of AEA's containing phosphinic acid and/or sulfonic acid delivery enhancing groups, are polymers and copolymers containing units or moieties derived from the polymerization of vinyl or allyl phosphinic and/or sulfonic acids substituted as needed on the 1 or 2 or 3 carbon atom by an organic retention-enhancing group, for example having the formula —(X)$_n$—R defined above. Mixtures of these monomers may be employed, and copolymers thereof with one or more inert polymerizable ethylenically unsaturated monomers such as those described above with respect to the operative synthetic anionic polymeric polycarboxylates.

As an example of a polymer containing repeating units in which one or more phosphonic acid delivery-enhancing groups are bonded to one or more carbon atoms in the polymer chain is poly(vinyl phosphonic acid) containing units of the formula:

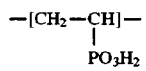   A.

which may be an AEA even though it does not contain a retention-enhancing group. A group of the latter type would however be present in poly (1-phosphonopropene) with units of the formula:

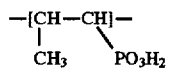   B.

A preferred phosphonic acid-containing polymer for use herein is poly (beta styrene phosphonic acid) containing units of the formula:

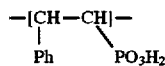   C.

wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of formula C alternating or in random association with units of formula I above, or poly (alpha styrene phosphonic acid) containing units of the formula:

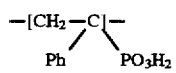   D.

in which the delivery- and retention-enhancing groups are terminally bonded to the chain.

These styrene phosphonic acid polymers and their copolymers with other inert ethylenically unsaturated monomers generally have molecular weights in the range of about 2,000 to about 30,000, preferably about 2,500 to about 10,000.

Other phosphonic-containing polymers include, for example, phosphonated ethylene having units of the formula:

   E.

where n may for example be an integer or have a value giving the polymer a molecular weight of for example about 3,000; and sodium poly (butene-4,4-diphosphonate) having units of the formula:

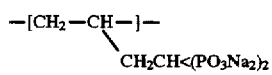

and poly(allyl bis (phosphonoethyl) amine) having units of the formula:

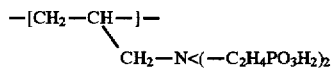   F.

Other phosphonated polymers, for example poly (allyl phosphono acetate), phosphonated polymethacrylate, etc. and the geminal diphosphonate polymers disclosed in EP Publication 0321233 are also useful in the practice of the present invention preferably provided that they contain or are modified to contain the above-defined organic retention-enhancing groups.

Polysiloxanes containing or modified to contain pendant delivery-enhancing groups and retention enhancing groups such as liquid silicone oils such as diphenyl or di (C$_1$-C$_4$) alkyl polysiloxanes and particularly dimethyl-polysiloxane, may also be employed in the practice of the present invention.

Also effective herein are ionomers containing or modified to contain delivery-and-retention-enhancing groups. Ionomers are described on pages 546–573 of the Kirk Othmer Encyclopedia of Chemical Technology, third edition, Supplement Volume, John Wiley & Sons, Inc. copyright 1984, which description is incorporated herein by reference. Also effective herein, provided they contain or are modified to contain retention-enhancing groups, are polyesters, polyurethanes and synthetic and natural polyamides including proteins and proteinaceous materials such as collagen, poly (arginine) and other polymerized amino acids.

The AEA, when employed, is incorporated in the compositions of the present invention in weight amounts of about 0.05 to about 5%, preferably about 0.1 to about 3%.

Linear molecularly dehydrated polyphosphate salts can be optionally employed herein as anticalculus agents. They are well known, being generally employed in the form of their wholly or partially neutralized water soluble alkali metal (e.g. potassium or preferably sodium) or ammonium salts, and any mixtures thereof. Representative examples include sodium hexametaphosphate, sodium tripolyphosphate, monosodium triacid,-, disodium diacid-, trisodium monoacid-, and tetrasodium-pyrophosphates, the corresponding potassium salts and the like. In the present invention, they can be employed in the oral compositions in approximate weight amounts of about 0.1 to 3%, typically 1 to 2.5%, more typically 1.5 to 2%, especially about 2%.

Particularly desirable anticalculus agents are tetraalkali metal pyrophosphates such as tetrasodium and tetrapotassium pyrophosphates, and mixtures thereof.

In the oral compositions, when both AEA and polyphosphate are present, the weight ratio of the AEA to polyphosphate ions is typically about 1.6:1 to about 2.7:1, preferably about 1.7:1 to about 2.3:1, more preferably about 1.9:1 to abut 2:1.

Fluoride ions may desirably also be included in the oral compositions of this invention, being in effect multifunctional in providing an anticaries effect or tooth-hardening effect and, in optional conjunction with the AEA, in inhibiting the salivary enzymatic hydrolysis of the polyphosphate anticalculus agent, when employed.

An amount of a source of fluoride ions, or fluorine-providing component, may be included to provide or supply about 25 ppm to 5,000 ppm of fluoride ions.

These compounds may be slightly soluble in water or may be fully water-soluble. They are characterized by their ability to release fluoride ions in water and by substantial freedom from undesired reaction with other compounds of the oral composition. Among these materials are inorganic fluoride salts, such as soluble alkali metal, alkaline earth metal salts, for example, sodium fluoride, potassium fluoride, ammonium fluoride, calcium fluoride, a cuprous fluoride, zinc fluoride, barium fluoride, sodium monofluorophosphate, aluminum mono- and di-fluorophosphate and sodium calcium fluorophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral composition, but it must be a non-toxic amount, generally about 0.0005 to about 3.0% in the preparation. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the composition, and preferably in the amount of about 0.05% to 1%, more typically about 0.2 to 0.35% for sodium fluoride. In the case of sodium monofluorophosphate, the compound may be present in an amount of about 0.1–3%, more typically about 0.76% by weight.

The oral composition of the present invention may be a solution of ingredients such as a mouthrinse or it maybe a semi-solid such as a toothpaste or gel dentifrice which may contain 0 to 75% of polishing agent, or chewing gum or solid lozenge or the like.

Oral gel preparations contain a siliceous polishing material including crystalline silica having particle sizes of up to about 5 microns, silica gel, colloidal silica or complex amorphous alkali metal aluminosilicate.

When visually clear or opacified gels are employed, a polishing agent of colloidal silica, such as those sold under the trademark Sylox® as Silox 15, or under the trademark Syloid® as Syloid 72 and Syloid 74, or under the trademark Santocel® as Santocel 100, or under the trademark Zeodent® as Zeodent 113 or alkali metal aluminosilicate complexes (that is, silica containing alumina combined in its matrix) are particularly useful, since they are consistent with gel-like texture and have refractive indices close to the refractive indices of gelling agent-liquid (including water and/or humectant) systems commonly used in dentifrices.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15–40% by weight and glycerine, sorbitol and/or the alkylene glycol (preferably propylene glycol) typically total about 20–75% by weight of the oral composition, more typically about 25–60%.

When the oral composition is substantially semi-solid or pasty in character, such as a toothpaste (dental cream), the vehicle of the dentifrice contains a dentally acceptable polishing material such as sodium bicarbonate or water insoluble polishing material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, silica, bentonite, and mixtures thereof with each other or with minor amounts of hard polishing materials such as calcined alumina and zirconium silicate. Preferred polishing materials include silica, insoluble sodium metaphosphate, dicalcium phosphate, calcium pyrophosphate and hydrated alumina, as well as sodium bicarbonate.

The polishing material is generally present in the gel, cream or paste compositions in weight concentrations of about 10% to about 75% by weight, preferably about 10% to about 30% in a gel and about 25% to about 75% in a cream or paste.

Toothpastes or dental cream dentifrices as well as gel dentifrices typically contain a natural or synthetic thickener or gelling agent in proportions of about 0.1 to about 10%, preferably about 0.5 to about 5%.

Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10–30% by weight. Mouthrinses typically contain about 50–85% of water, about 0 to 20% by weight of a non-toxic alcohol and about 10–40% by weight of the humectant.

Organic surface-active agents are used in the compositions of the present invention to achieve increased prophylactic action, assist in achieving thorough and complete dispersion of the AA throughout the oral cavity, and render the instant compositions more cosmetically acceptable. The organic surface-active material is preferably anionic, non-ionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines. The use of these sarcosinate compounds in the oral compositions of the present invention is often advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic® materials).

Examples of polyoxamers useful in the practice of the present invention include block copolymers of polyoxyethylene and polyoxypropylene having an average molecular weight from about 3000 to 5000 and a preferred average molecular weight from about 3500 to about 4000 and containing about 10–80% hydrophilic polyoxyethylene groups, by weight, of the block copolymer. A preferred polyoxamer useful in the practice of the present invention is Pluronic F127 (trademark) a block copolymer of polyoxyethylene and polyoxypropylene having a molecular weight of about 4000.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Agents used to diminish teeth sensitivity such as strontium chloride, potassium nitrate and potassium citrate can also be included in the oral compositions of the present invention at concentrations of about 0.1 about 10% by weight.

Various other materials may be incorporated in the oral compositions of this invention including whitening agents such as urea peroxide and hydrogen peroxide, preservatives, such as sodium benzoate, chlorophyll compounds and/or ammoniated material such as urea, diammonium phosphate, and mixtures thereof. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the AA is dispersed in a mixture of ingredients, e.g. alcohol, humectants, surfactants, and AEA and salts such as sodium fluoride and potassium phosphate, and flavor are then added and mixed. The ingredients are then mixed under vacuum for about 15–30 minutes. The resulting rinse is then packaged. Dentifrices are prepared similarly, the additional thickener and polishing agents being included in the last or penultimate step.

In the preferred practice of this invention an oral composition according to this invention such as a dentifrice is preferably applied as by brushing regularly to dental enamel, such as every second or third day or preferably from 1 to 3 times daily, at a pH of about 4.5 to 10, generally about 5.5 to 9, preferably about 6 to 8, for at least 2 weeks up to 8 weeks or more up to lifetime. The dentifrice is typically removed by rinsing with water after each application. Mouthrinses are rinsed or gargled in similar systematic manner.

The compositions of this is invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrolysate, Lycasin, hydrogenated glucose, hydrogenated disaccharides or hydrogenated polysaccharides, in an amount of about 90 to 98% by weight of the total composition. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax®.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose, Gantrez®, and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

In Table I below following illustrative Example 6, categories of AA's are listed. Category I sets forth AA's which are indicated to be 100 or more times more active than thymol. That is, they would be comparable to or even more effective than triclosan in antiplaque activity. Category II sets forth AA's which are lower in activity, e.g. 10 to 50 times than the activity of thymol.

A further aspect of this invention relates to compounds of this Category I which are characterized as having one of the following formulae:

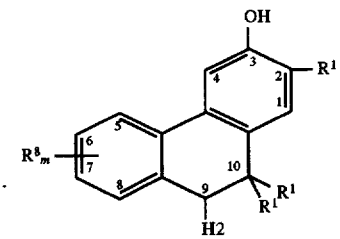

III.

or

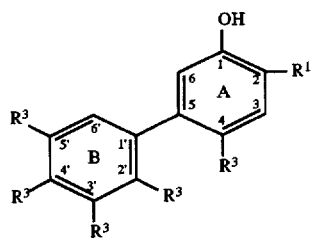

IV.

wherein $R^1$ is (1) a $C_{1-8}$ n-alkyl, partially or fully substituted with $C_{3-6}$ cycloalkyls or $C_{1-7}$ side chain alkyls or (2) a $C_{3-6}$ cycloalkyl, optionally partially or fully substituted with $C_{1-7}$ side chain alkyls or $C_{3-6}$ cycloalkyls; and each $R^3$ is independently hydrogen or $R^1$, with the proviso that when $R^3$ in the A ring of formula IV is hydrogen at least one $R^3$ in the B ring is $R^1$; and $R^8$ in Formula III is independently H or $R^1$ in the 5, 6, 7 and/or 8 positions and m is 4.

A preferred compound of formula III is 2-t-butyl-3-hydroxy-10,10-dimethyl-9,10-dihydrophenanthrene. Preferred compounds of formula IV are:

2-t-butyl-5-(4'-t-butylphenyl)phenol;
2,4-di-t-butyl-5-phenyl phenol; and
2-t-butyl-4-(1,1-dimethylpropyl)-5-phenyl phenol General Synthetic Procedure for the Alkylated Phenol Antibacterial Agents Employed Herein The AA's of this invention, some of which may be found in nature, are made synthetically by Friedel-Crafts alkylation in accordance with typical methods of synthetic organic chemistry. Thus, a phenolic compound, e.g. phenol, 3-phenylphenol, 4-phenylphenol, or 9,10-dihydro-3-hydroxy-10,10-dimethylphenanthrene, is treated with RX, where R is an alkyl moiety and X is halide or other appropriate leaving group, in the presence of a suitable Friedel-Crafts catalyst, e.g. aluminum chloride or ferric chloride, either neat or in a suitable solvent, e.g. methylene chloride, carbon disulfide, or nitrobenzene. Treatment of a phenolic compound with one equivalent of RX results in predominantly mono alkyl substitution ortho to the phenol hydroxyl. Treatment of a phenolic compound with two or more equivalents of RX results in di- or polyalkyl-phenols. Multiple alkylation can also be done stepwise. Unsymmetricaly substituted polyalkylphenols may be obtained by starting with a 3-alkylphenol. It is noteworthy that in dialkylating biphenylphenols with bulky alkyls, e.g. t-butyl, the first alkyl is introduced ortho to the hydroxyl while the second alkyl substitution occurs on the pendant phenyl. These methods are illustrated by the syntheses of 2-tert-butyl-5-phenylphenol and 2-tert-butyl-5-(4-tert-butylphenyl)phenol, shown below as Examples 1 and 2, respectively.

In order to obtain 2,4-di-tert-butyl-5-phenylphenol, 3-nitrophenylphenol is alkylated with two moles of t-butyl chloride according to the method described above. The nitro group of the resulting 2,4-di-tert-butyl-5-nitrophenylphenol is removed by catalytic hydrogenation, followed by diazotization and reduction of the diazonium salt of the aniline*.

* See N. Porowska, W. Polaczkowa, and S. Kwiatkowska, Rocz. Chem., 44 (2), 375 (1970).

Ortho, meta, and para mono n-alkyl substituted phenols are preferably obtained, as follows. The alkyl halide R'X, where R' is one methylene group shorter than the desired alkyl chain R, is reacted with magnesium to form the corresponding Grignard R'MgX. This is reacted with o-, m-, or p-anisaldehyde to yield a 2-hydroxyalkyl anisole. The hydroxy group is removed by hydrogenolysis over palladium on carbon in refluxing cyclohexene to give the n-alkyl substituted anisole. The desired n-alkyl substituted phenol is generated by cleavage of the methyl group from the anisole by treatment with boron tribromide°.

°J. Weinstock, et. al., J. Med. Chem., 30, 1166 (1987).

Similar alkylation can be accomplished by substitution of RX in the foregoing description with an appropriate olefin.

The SIKT (Short Interval Kill Test) test referred to in the examples is used to assess the ability of actives to kill in a short period of time (e.g. 2 minutes), simulating antiplaque mouthrinse conditions. In this test, which is described in U.S. Pat. No. 5,275,805, column 11, lines 10–28, which description is herewith incorporated herein, control and test samples are mixed with pre-determined innoculums of S. sanguis, S. mutans and S. viscosus ($10^6$–$10^7$ Colony forming unit (cfu/ml.) for 2 minute contact times, the systems then neutralized to inhibit further antibacterial activity, and the surviving bacteria enumerated using plate count methodology. The reduction in cfu counts compared to the water control is the basis for expressing the antibacterial activity of the test agents, i.e. as % killing in comparison to the appropriate placebo or control.

The MIC (Minimum Inhibitory Concentration) test referred to in the examples measures the minimum concentration in ppm or mM of the AA at which the growth of the bacteria (same 3 plaque involved species as employed in the SIKT tests) is completely inhibited by the AA. The smaller the MIC, the greater the antibacterial activity of the AA being tested. This MIC test is also described in U.S. Pat. No. 5,275,805 at column 11, lines 54–68, which description is herewith incorporated herein.

The following examples are further illustrative of the nature of the present invention, but it is understood that the invention is not limited thereto. All amounts and proportions referred to herein and in the appended claims are by weight unless otherwise indicated.

EXAMPLE 1

2-tert-butyl-5-phenylphenol (3-hydroxy-4-butyl-biphenyl)

A suspension of 0.8 aluminum chloride in 50 mL of anhydrous methylene choloride is stirred under an anhydrous nitrogen atmosphere at 5°–15° C. while a solution of 17 g of 3-phenylphenol and 24 mL of t-butylchloride in 50 mL of anhydrous methylene chloride is added dropwise. The resultant mixture is stirred for 2 hours, then allowed to stand at room temperature for 12 hours. The reaction mixture is poured over 150 g of ice/water and shaken. The organic phase is separated and the aqueous remainder is twice extracted with 50 mL portions of methylene chloride. The combined organic solutions are washed twice with 50 mL portions of water, 50 mL of saturated aqueous sodium chloride solution, rendered anhydrous over sodium sulfate, filtered, and evaporated in vacuo. The residue is taken into about 150 mL of hexane. Upon standing at room temperature, 3-hydroxy-4-t-butylbiphenyl crystallizes from the solution. This is isolated by filtration and successively recrystallized from 100 mL portions of pentane until its melting point becomes constant. The material is obtained as a white crystalline compound in 6.8 g yield, m.p. 86°–87° C. The original hexane filtrates also produce another crop of crystals which provides 1.1 g of 2-tert-butyl-5-(4'-tert-butylphenyl) phenol, m.p. 143°–145° C. after several recrystalizations from pentane. An additional 1.12 g of this material are obtained from the chromatography of the mother liquor residues.

EXAMPLE 2

Mouth formulation containing 3-hydroxy-4,4'-di-t-butyl biphenyl (2-t-butyl-5(4'-t.butylphenyl)phenol)

| Ingredients | % |
|---|---|
| Sorbitol (70%) | 10.00 |
| Glycerin (99.7%) | 10.00 |
| Ethanol (95%) | 15.00 |
| Propylene glycol | 15.00 |
| Sodium lauryl sulfate | 0.50 |
| Tauranol (97%)* | 0.25 |
| Pluronic F127** | 0.25 |
| Mint flavor | 0.10 |
| 3-hydroxy-4,4'-di-t-butyl biphenyl | 0.30 |
| Water | 48.60 |
| Total | 100.00 |

*Sodium methyl cocoyl taurate, trademark.
**Block copolymer polyoxypropylene/polyoxyethylene, M.W. 4000, trademark.

EXAMPLE 3

Toothpaste formulation containing 3-hydroxy-4,4'-di-t-butyl biphenyl

| Ingredients | % |
|---|---|
| 3-hydroxy-4,4'-di-t-butyl biphenyl | 0.30 |
| Sodium monofluorophosphate | 0.19 |
| Propylene glycol | 30.00 |
| Glycerin (99.7%) | 10.00 |
| Zeodent 115* | 20.00 |
| Sorbitol (70%) | 25.00 |
| Water | 7.61 |
| Sylodent 15** | 2.00 |
| Sodium lauryl sulfate | 0.50 |
| Pluronic F127 | 0.50 |
| Tauranol (97%) | 0.50 |
| Flavor | 1.00 |
| $K_2HPO_4$ | 0.50 |
| Sodium carboxymethyl cellulose | 0.80 |
| Titanium dioxide | 0.50 |
| Iota-carrageenan*** | 0.30 |
| Sodium saccharin | 0.30 |
| Total | 100.00 |

*Silica polishing agent, trademark.
**Silica thickener, trademark.
***Thickener, stabilizer.

The above formulation can be modified by replacing some or all Zeodent 115 silica polishing agent and Sylodent 15 silica thickener with sodium bicarbonate, insoluble sodium metaphosphate, dicalcium phosphate, calcium pyrophosphate, hydrated alumina and mixtures thereof.

In the following Examples 4 and 5 the tests are carried out in neat solutions of the AA active agent in 98.5% ethanol (EtOH) which, at the test concentrations, does not show any antibacterial properties.

EXAMPLE 4

2-tert-butyl-5-phenyl phenol and 2-tert-butyl-5-(4'-tert-butylphenyl) phenol are tested in vitro against several strains of bacteria typically found in human dental plaque. Experimental results are given below

| Minimum Inhibitory Concentration (MIC) Results | | | |
|---|---|---|---|
| | Bacterial species (MIC in ppm) | | |
| | *A. viscosus* | *S. sanguis* | *S. mutans* |
| (1)2-t-butyl-5-(4'-t-butylphenyl)phenol | 0.061 | 0.0305 | 0.122 |
| (2)2-t-butyl-5-phenylphenol | 0.976 | 0.976 | 0.976 |
| Thymol | 31.25 | 62.5 | 31.25 |
| Triclosan | 0.976 | 1.95 | 1.92 |

This test shows agent (1) to be substantially more active than any of the other agents, and agent (2) to be significantly more active than triclosan against *S. sanguis* and *S. mutans* and many times superior to thymol against all three strains.

EXAMPLE 5

SIKT test results (neat solutions of 3-hydroxy-4,4'-di-t-butyl biphenyl=2-t-butyl-5 (4'-t-butylphenyl)phenol) against *A. viscosus*.

| Agent | % killing vs. placebo |
|---|---|
| 0.03% Triclosan | 21.0 |
| 0.03% 3-hydroxy-4,4' di-t-butylbiphenyl | 58.5 |

Each AA compound is formulated in 98.5% EtOH. At the concentrations present in the final test solutions the EtOH does not show any antibacterial properties by itself. The placebo is a formulation that contains no active agents, e.g. only EtOH. These tests show applicants' AA to have more than twice the antibacterial activity of triclosan against *A. viscosus*.

The following Table I lists preferred AA's of this invention in two categories. Predicted MIC's in mM are indicated as well as found values for several of them. In addition, MIC's of thymol and triclosan are set forth.

Predicted values are based on our above-referred to findings and other criteria including consideration of types, sizes, numbers and positions of substituents, their structure (straight, branched, cyclic alkyl), etc. Listed in Category I are novel compounds within the scope of formulas II and IV above, having predicted antibacterial activities 100× thymol and MIC's below about 0.4 mM. Listed in Category II are compounds, some of which are known, having predicted activities 10–50× tymol and MIC's above about 0.04 mM. Experimental ("Found") MIC's of one AA in Category I and two in Category II support relatively conservatively predicted values in being substantially equal to or substantially lower (e.g. 0.0022 vs. 0.038 in Category I and 0.043 vs. 0.12 in Category II) and hence even substantially more antimicrobial against A. viscosis than predicted. The Table also shows that all listed AA's have substantially lower predicted and found MIC's than thymol, that the found MIC of category II AA compound 2-t-butyl-4-(4'-t-butylphenyl)phenol is about one-tenth that of triclosan, and that the predicted MIC's of 2,4-di-t-butyl-5-phenylphenol and 2-t-butyl-4-(1,1-dimethylpropyl)-5-phenylphenol) are even lower than that of the 2-t-butyl-4-(4-t-butylphenyl)phenol and comparable to the MIC of triclosan.

TABLE I

| Phenol | MIC (mM) v A. viscosus | |
|---|---|---|
| | Predicted | Found |
| Thymol | 1.7 | 2.0 |
| Triclosan | — | 0.02 |
| Category I (Predicted 100X thymol) | | |
| 2-t-butyl-5-(4'-t-butylphenyl) | 0.038 | 0.0022 |
| 2,4-di-t-butyl-5-phenyl | 0.025 | |
| 2-t-butyl-4-(1,1-dimethylpropyl)-5-phenyl | 0.031 | |
| 2-t-butyl-3-hydroxy-10,10-dimethyl-9,10-dihydrophenanthrene | 0.038 | |
| Category II (Predicted 10–50X thymol) | | |
| 2-t-butyl-4-(4'-t-butylphenyl) | 0.16 | |
| 2-t-butyl-4-phenyl | 0.12 | |
| 2-t-butyl-5-phenyl | 0.12 | 0.043 |

This invention has been disclosed with respect to preferred embodiments thereof and it will be understood that variations and modifications obvious to those skilled in the art are intended to be included within the purview of this application and the scope of the appended claims.

We claim:

1. An oral composition which is a mouthrinse or a semi-solid toothpaste or gel dentifrice comprising an orally acceptable mouthwash vehicle comprising a water-alcohol mixture or dentifrice vehicle comprising a water phase with humectant and a dentally acceptable polishing material and an effective antiplaque amount of at least one substantially water insoluble noncationic antibacterial agent (AA) of the formula:

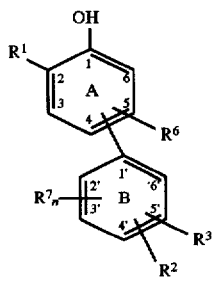

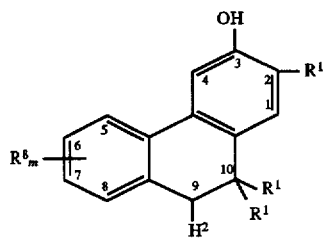

wherein $R^1$ is (1) a $C_{1-8}$ n-alkyl, optionally partially or fully substituted with $C_{3-6}$ cycloalkyls or $C_{1-7}$ side chain alkyls, or (2) a $C_{3-6}$ cycloalkyl, optionally partially or fully substituted with $C_{1-7}$ side chain alkyls or $C_{3-6}$ cycloalkyls;

the B ring and $R^6$ of formula I are interchangeably substituted in the 4 and 5 positions of the A ring of formula I, and $R^6$ is H or $R^1$; and (1) $R^2$ and $R^3$ are interchangeably substituted in the 4' and 5' positions of the B ring of formula I, and $R^2$ is $R^1$ and $R^3$ is H or $R^1$; or (2) in the B ring, $R^3$ in the 5<<-position is H, $R^2$ in the 4<< position is $R^7$, $R^7$ is independently H or $R^1$ in the 2' and/or 3' positions, and n is 2; and $R^8$ in formula III is independently H or $R^1$ in the 5, 6, 7 and/or 8 positions and m is 4.

2. A composition according to claim 1 wherein the AA has formula I wherein $R^1$ is t-butyl.

3. A composition according to claim 2 wherein one of $R^2$ and $R^3$ has an $R^1$ value and the other is H.

4. A composition according to claim 3 wherein the AA comprises 2-t-butyl-5-phenyl phenol.

5. A composition according to claim 3 wherein the AA comprises 2-t-butyl-4-phenyl phenol.

6. A composition according to claim 3 wherein the AA comprises 2-t-butyl-5-(4'-t-butyl phenyl) phenol.

7. A composition according to claim 3 wherein the AA comprises 2-t-butyl-4-(4'-t-butyl phenyl) phenol.

8. A composition according to claim 3 wherein the AA comprises 2,4-di-t-butyl-5-phenyl phenol.

9. A composition according to claim 3 wherein the AA comprises 2-t-butyl-4-(1,1-dimethylpropyl)-5-phenyl phenol.

10. A composition according to claim 1 wherein the AA has formula III and $R^1$ in the 2-position is t-butyl.

11. A composition according to claim 10 wherein the $R^1$'s in the 10-position are lower C1–6 alkyl.

12. A composition according to claim 11 wherein the AA comprises 2-t-butyl-3-hydroxy-10,10-dimethyl-9,10-dihydrophenanthene.

13. A composition according to claim 1 wherein $R^1$ and $R^4$ in ortho position to the OH group, and $R^2$ in the 4' position in the B ring of formula I, are t-butyl.

14. A composition according to claim 1 further containing about 0.05–5% of antibacterial-enhancing agent (AEA).

15. A composition according to claim 14 wherein said AEA has an average molecular weight (M.W.) of about 100 to about 5,000,000.

16. A composition according to claim 15 wherein said AEA contains at least one acidic delivery-enhancing group and at least one organic retention-enhancing group.

17. A composition according to claim 16 wherein said delivery-enhancing group comprises carboxylic, phosphonic, phosphinic and/or sulfonic acid groups and salts and any mixtures thereof, and said organic retention-enhancing group has the formula —$(X)_n$—R wherein X is O, N, S, SO, $SO_2$, P, PO or Si, R is hydrophobic alkyl, alkylene, acyl, aryl, alkaryl, aralkyl, heterocyclic, or their inert-substituted derivatives, and n is 1 or zero.

18. A composition according to claim 17 wherein said AEA is an anionic polymer containing a plurality of said delivery-enhancing and retention-enhancing groups.

19. A composition according to claim 18 wherein said delivery-enhancing group comprises carboxylic or salt thereof.

20. A composition according to claim 19 wherein said AEA is a copolymer of maleic acid or anhydride with another ethylenically unsaturated polymerizable monomer.

21. A composition according to claim 20 wherein said other monomer is methyl vinyl ether in a 4:1 to 1:4 molar ratio with the maleic acid or anhydride, and said copolymer has an average M.W. of about 70,000 to 250,000 and comprises about 0.05–3% of the composition.

22. A composition according to claim 18 wherein said delivery-enhancing group comprises phosphonic or salt thereof.

23. A composition according to claim 22 wherein said AEA comprises poly (beta-styrenephosphonic acid) or poly (alpha-styrenephosphonic acid) or a copolymer of either styrenephosphonic acid with another ethylenically unsaturated monomer.

24. A composition according to claim 1 further containing an effective anticalculus amount of at least one linear molecularly dehydrated polyphosphate anticalculus agent.

25. A composition according to claim 24 containing about 0.1 to 3% of said polyphosphate and the weight ratio of said AEA to polyphosphate ion ranges from about 1.6:1 to about 2.7:1.

26. A composition according to claim 25 wherein said polyphosphate comprises tetrasodium or tetrapotassium pyrophosphate or a mixture thereof.

27. A composition according to claim 14 further containing an effective anticalculus amount of at least one linear molecularly dehydrated polyphosphate anticalculus agent.

28. A composition according to claim 17 further containing an effective anticalculus amount of at least one linear molecularly dehydrated polyphosphate anticalculus agent.

29. A composition according to claim 1 further containing about 25–5,000 ppm of fluoride ions.

30. A composition according to claim 14 further containing about 25–5,000 ppm of fluoride ions.

31. A composition according to claim 27 further containing about 25–5,000 ppm of fluoride ions.

32. A composition according to claim 1 wherein the AA has a molecular weight of about 175 to about 500.

33. A composition according to claim 1 wherein the AA has a molecular weight of about 210 to about 310.

34. A composition according to claim 1 wherein said composition is a dentifrice containing about 10% to about 75% by weight of a dentally acceptable polishing agent.

35. A composition according to claim 34 wherein said polishing agent is silica.

36.

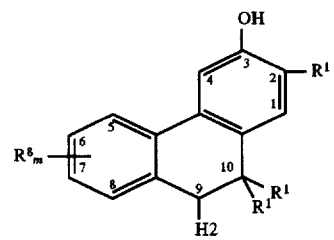

or

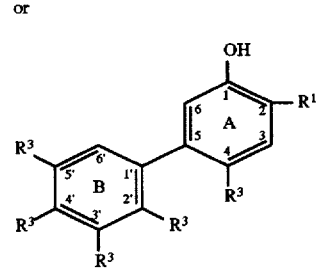

wherein $R^1$ is (1) a $C_{1-8}$ n-alkyl, partially or fully substituted with $C_{3-6}$ cycloalkyls or $C_{1-7}$ side chain alkyls or (2) a $C_{3-6}$ cycloalkyl, optionally partially or fully substituted with $C_{1-7}$ side chain alkyls or $C_{3-6}$ cycloalkyls; and each $R^3$ is independently hydrogen or $R^1$, with the proviso that when $R^3$ in the A ring of formula IV is hydrogen at least one $R^3$ in the B ring is $R^1$; and $R^8$ in Formula III is independently H or $R^1$ in the 5, 6, 7 and/or 8 positions and m is 4.

37. A compound according to claim 36 of formula IV.

38. A compound according to claim 37 wherein $R^1$ is t-butyl.

39. A compound according to claim 38 wherein said compound is 2-t-butyl-5-(4'-t-butylphenyl)phenol.

40. A compound according to claim 38 wherein said compound is 2,4-di-t-butyl-5-phenyl phenol.

41. A compound according to claim 38 wherein said compound is 2-t-butyl-4-(1,1-dimethylpropyl)-5-phenylphenol.

42. A compound according to claim 36 of formula III.

43. A compound according to claim 42 wherein $R^1$ in the 2 position is t-butyl.

44. A compound according to claim 43 wherein said compound is 2-t-butyl-3-hydroxy-10,10-dimethyl-9,10-dihydrophenanthrene.

45. A method for inhibiting dental plaque comprising applying to the teeth plaque-inhibiting amount of an oral composition as defined in any one of claims 1 or 2–30.

46. The oral composition as defined in any one of claims 1 or 2–35 wherein said AA is present in amount of about 0.003–5%.

* * * * *

UNITED STATES PATENT AND TRADEMARK OFFICE
CERTIFICATE OF CORRECTION

PATENT NO. : 5,723,500

DATED : March 3, 1998

INVENTOR(S) : Orum D. Stringer et al.

It is certified that error appears in the above-identified patent and that said Letters Patent is hereby corrected as shown below:

On the title page please add the following inventor:

Stuart Shapiro, Kilchberg, Switzerland

Signed and Sealed this

First Day of September, 1998

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,723,500
DATED : March 3, 1998
INVENTOR(S) : Stringer, et al

It is certified that error appears in the above-identified patent and that said Letters Patent is hereby corrected as shown below:

At column 20, line 1, should read: 36. A compound characterized as having one of the following formulae:

Signed and Sealed this

Twenty-seventh Day of April, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,723,500
DATED : March 3, 1998
INVENTOR(S) : Orum D. Stringer et al.

It is certified that error appears in the above-identified patent and that said Letters Patent is hereby corrected as shown below:

Title page, insert the following item:
--[60] Provisional application No. 60/004,196, Sep. 22, 1995--

Column I, line 3, insert --This application claims the benefit of U.S. Provisional Application no.: --60/004,196 filed Sep. 22, 1995.--

Signed and Sealed this

Tenth Day of August, 1999

Attest:

*Attesting Officer*

Q. TODD DICKINSON

*Acting Commissioner of Patents and Trademarks*